United States Patent
Schneiderman et al.

(10) Patent No.: US 7,332,467 B2
(45) Date of Patent: Feb. 19, 2008

(54) HYDROPHILICALLY MODIFIED POLYOLS FOR IMPROVED HYDROPHOBIC SOIL CLEANING

(75) Inventors: Eva Schneiderman, Mason, OH (US); Jun Ma, Beijing (CH); Kevin Todd Norwood, Cincinnati, OH (US); Randy Thomas Reilman, Cincinnati, OH (US); Julie Ann Menkhaus, Cleves, OH (US); Jeffrey John Scheibel, Loveland, OH (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/303,684

(22) Filed: Dec. 16, 2005

(65) Prior Publication Data

US 2006/0135395 A1    Jun. 22, 2006

Related U.S. Application Data

(60) Provisional application No. 60/637,205, filed on Dec. 17, 2004.

(51) Int. Cl.
C11D 1/16 (2006.01)
C11D 1/83 (2006.01)
C11D 1/86 (2006.01)

(52) U.S. Cl. ............... 510/427; 510/235; 510/289; 510/290; 510/340; 510/351; 510/356; 510/504; 510/421; 510/422; 510/426; 510/428

(58) Field of Classification Search ............... 510/235, 510/289, 290, 340, 351, 356, 427, 504, 421, 510/422, 426, 428
See application file for complete search history.

(56) References Cited

U.S. PATENT DOCUMENTS

| | | | |
|---|---|---|---|
| 4,347,168 A | 8/1982 | Murphy et al. | |
| 4,661,228 A | 4/1987 | Rubingh et al. | |
| 4,746,456 A | 5/1988 | Kud et al. | |
| 4,814,102 A | 3/1989 | Baur et al. | |
| 4,846,994 A | 7/1989 | Kud et al. | |
| 4,849,126 A | 7/1989 | Kud et al. | |
| 4,904,408 A | 2/1990 | Kud et al. | |
| 4,906,397 A * | 3/1990 | Leighton et al. | 510/361 |
| 4,908,150 A | 3/1990 | Hessel et al. | |
| 5,049,302 A | 9/1991 | Holland et al. | |
| 5,070,140 A | 12/1991 | Lind et al. | |
| 5,082,585 A | 1/1992 | Hessel et al. | |
| 5,156,906 A | 10/1992 | Holland | |
| 5,281,355 A * | 1/1994 | Tsaur et al. | 510/393 |
| 5,318,719 A | 6/1994 | Hughes et al. | |
| 5,371,119 A | 12/1994 | Bohlander et al. | |
| 5,635,554 A | 6/1997 | Boeckh et al. | |
| 5,672,761 A | 9/1997 | Adkins et al. | |
| 5,733,856 A | 3/1998 | Gopalkrishnan et al. | |
| 5,750,483 A | 5/1998 | Welch et al. | |
| 5,994,285 A * | 11/1999 | Sachdev et al. | 510/329 |
| 5,998,357 A | 12/1999 | Appel et al. | |
| 6,083,488 A | 7/2000 | Riccobono et al. | |
| 6,159,918 A * | 12/2000 | Bae-Lee et al. | 510/293 |
| 6,271,307 B1 | 8/2001 | Huff et al. | |
| 6,315,835 B1 | 11/2001 | Kerobo et al. | |
| 6,444,633 B2 | 9/2002 | Price | |
| 6,579,839 B2 | 6/2003 | Price et al. | |
| 6,579,953 B1 | 6/2003 | Gotsche et al. | |
| 2001/0036471 A1 | 11/2001 | Angel et al. | |
| 2003/0186833 A1 | 10/2003 | Huff et al. | |
| 2003/0224025 A1 | 12/2003 | Gotshe et al. | |
| 2004/0068051 A1 | 4/2004 | Ortiz et al. | |
| 2004/0097657 A1 | 5/2004 | Morschhaeuser et al. | |
| 2004/0121928 A1 | 6/2004 | Price et al. | |
| 2005/0113280 A1 | 5/2005 | Reddy et al. | |
| 2005/0153860 A1 * | 7/2005 | Zhou et al. | 510/392 |
| 2005/0153867 A1 * | 7/2005 | Scheibel et al. | 510/499 |
| 2005/0170987 A1 * | 8/2005 | Scheibel et al. | 510/376 |
| 2005/0187133 A1 * | 8/2005 | Schneiderman et al. | 510/475 |
| 2005/0209125 A1 | 9/2005 | Song et al. | |

FOREIGN PATENT DOCUMENTS

| | | |
|---|---|---|
| DE | 34 13 566 A1 | 10/1985 |
| EP | 288067 | 10/1988 |
| EP | 325054 | 7/1989 |
| EP | 358474 | 3/1990 |
| JP | 10-081744 | 3/1998 |
| JP | 10-140182 | 5/1998 |
| WO | WO 95/22593 | 8/1995 |
| WO | WO 01/05874 A1 | 1/2001 |
| WO | WO 01/79408 A1 | 10/2001 |

(Continued)

OTHER PUBLICATIONS

U.S. Appl. No. 11/015,574, filed Dec. 17, 2004, Scheibel et al.

(Continued)

*Primary Examiner*—Charles Boyer
(74) *Attorney, Agent, or Firm*—Stephen T. Murphy; Kim W. Zerby; Steve W. Miller

(57) ABSTRACT

A hydrophilically modified polyol compounds, compositions including the hydrophilically modified polyol compounds and methods of using such compositions and process of making such compositions for anti-redeposition and hydrophobic soil cleaning benefits.

21 Claims, No Drawings

FOREIGN PATENT DOCUMENTS

| | | |
|---|---|---|
| WO | WO 01/98388 A1 | 12/2001 |
| WO | WO 02/11686 | 2/2002 |
| WO | WO 03/010256 | 2/2003 |
| WO | WO 2005/063847 A | 7/2005 |
| WO | WO 2005/063848 A | 7/2005 |
| WO | WO 2005/078060 A | 8/2005 |

OTHER PUBLICATIONS

U.S. Appl. No. 11/300,714, filed Dec. 15, 2005, Carter et al.
U.S. Appl. No. 11/303,689, filed Dec. 15, 2005, Schneiderman et al.

* cited by examiner

HYDROPHILICALLY MODIFIED POLYOLS FOR IMPROVED HYDROPHOBIC SOIL CLEANING

CROSS REFERENCE TO RELATED APPLICATION

This application claims priority under 35 U.S.C. § 119(e) to U.S. provisional application No. 60/637205, filed Dec. 17, 2004.

FIELD OF THE INVENTION

The present invention relates to a composition having a hydrophilically modified polyol compound, most preferably having zwitterionic character and a surfactant system for improved hydrophobic soil cleaning and (anti-redeposition) graying prevention.

BACKGROUND OF THE INVENTION

Efficient cleaning of hydrophobic soils such as grease, oil, body soils, hydrophobic particulates (e.g. soot, dust, etc . . . ), and some hydrophilic soils (such as clays) continues to be a challenge for detergent formulators, especially in regions where hand washing and colder water conditions exist. Many consumers in these regions may use hand washing process in addition to automating washing machines. The washing process in these regions will comprise the steps of soaking, pre-washing, pre-treating, and re-using of wash water. Often, wash water in the hand wash process is cold and may be high in impurities, such as hardness, concentration of transition metals and amounts of soil and particulates. All of these factors result in what is referred to as "stressed wash conditions", primarily in the amount of the soil, hardness, and particulates in the re-used wash water. These wash conditions are different from typical granular laundry detergents similar to those often found in the United States or the European Union via primary use of automatic washing machines.

Therefore, a problem associated with stressed wash conditions is the inefficient cleaning in the re-used wash water, resulting in graying of the white and light fabric items in the wash due to the deposition of the soil and particulates. Another problem associated with stressed wash conditions is the decreased level of hydrophobic soil cleaning and particulate soil cleaning due to the used-up surfactant system, high soil-load, higher hardness and colder wash temperatures. These problems are particularly accentuated in the re-use of wash water.

There are some known polymers for improved clay and hydrophilic soil cleaning and prevention of graying white and light fabric items in the wash. These include those polymers described in U.S. Pat. No. 4,661,288; U.S. Pat. No. 6,444,633; U.S. Pat. No. 6,579,839 and WO 01/05874. It is also known that some polymers can improve cleaning of other soils, such as those discussed in WO 01/79408 A1.

Polyol compounds such as sugar based materials are sustainable and readily available raw materials that lend themselves to be broadly tuned to address specific formulability and performance requirements. Specific performance requirements include the prevention of graying of white and light fabric items and providing cleaning of hydrophobic soils (grease, oil, body soils, soot, etc . . . ) under hand washing conditions having high soil and high hardness. Other performance requirements include use in automatic and hand-dishwashing compositions, surface cleaning compositions, such as floor cleaners, wood, ceramic tile, linoleum, cleaners, personal care compositions, such as shampoos, hair conditioners, soaps, and body washes, and pet cleaning care compositions, such as dog and cat shampoos.

Formulability of some of the current commercial polymers, which provide cleaning of grease and oil soils, into granular and liquid laundry detergents, hard surface cleaners, dish cleaning compositions, personal care compositions, and pet cleaning compositions continues to challenge detergent formulators.

SUMMARY OF THE INVENTION

The present invention relates to a composition comprising: A composition comprising: (a) from about 0.005% to about 30% of one or more hydrophilically modified polyol compounds comprising from 5 to 11 hydroxy moieties wherein at least one hydroxy moiety further comprises one or more ethoxy moiety; the one or more ethoxy moiety further comprising an anionic capping unit, a cationic capping unit, or a mixture thereof; wherein the overall average charge on the hydrophilically modified polyol compound is about −4 to about +4; and (b) a surfactant system comprising from about 9% to about 25% by weight of the composition of $C_{10}$-$C_{15}$ linear alkyl benzene sulfonate and from 0% to about 7% by weight of the composition of a co-surfactant selected from nonionic surfactants, anionic surfactants, cationic surfactants, and mixtures thereof.

The present invention further relates to methods of using such compositions and processes of making such compositions. The present invention further relates to hydrophilically modified polyol compounds.

DETAILED DESCRIPTION OF THE INVENTION

There exists a need for compositions comprising materials that are relatively easy to manufacture from sustainable and readily available raw materials, which may be broadly tuned to address specific formulability and performance requirements. The selection of suitable materials is dependent upon the other components of the composition, performance requirements, processing requirements, washing conditions, and consumer habits involved in the use of the cleaning compositions.

Tunable polymers such as hydrophilically modified polyol compounds are believed to be agents that strengthen performance of compositions for cleaning and are believed to be effective in stressed wash conditions, in which surfactant alone is not capable of efficient cleaning and preventing graying of white and light fabric items and delivering desired hydrophobic soil cleaning. It should be noted however that hydrophilically modified polyol compounds use is not limited by the stressed wash conditions, but also hydrophilically modified polyol compounds may add to performance benefits in the non-stressed wash conditions.

It is believed, without being limited by a theory that the tunability of the polymer structure via modification of various molecular parameters in the system that enables use of the most suitable polymer for the desired application. Without being limited by a theory it is believed that the combination of the below described hydrophilically modified polyol compounds and below described surfactant systems enable very efficient particulate soil dispersion, it will contribute to prevention of soil redeposition, and will help in emulsifying hydrophobic soils such as oils on the presence of surfactants. In addition the hydrophilically modified polyol compounds alone as well as in the mixture with below described surfactant systems enable interactions with hydrophobic soils and enable more efficient delivery of surfactant to surfaces being cleaned.

As used herein "light-duty liquid dishwashing detergent composition" refers to those compositions that are employed in manual (i.e. hand) dishwashing. Such compositions are generally high sudsing or foaming in nature.

As used herein "laundry detergent composition" refers to those compositions that are employed in washing clothing and other fabrics and any solutions containing the composition in a diluted form. Such compositions are generally low sudsing or foaming in nature.

As used herein "shampoo" refers to those compositions that are employed in washing of hair of human and animals.

As used herein "body wash" refers to those compositions in liquid form used for cleaning skin surfaces.

Incorporated and included herein, as if expressly written herein, are all ranges of numbers when written in a "from X to Y" or "from about X to about Y" or "X-Y" format. It should be understood that every limit given throughout this specification will include every lower or higher limit, as the case may be, as if such lower or higher limit was expressly written herein. Every range given throughout this specification will include every narrower range that falls within such broader range, as if such narrower ranges were all expressly written herein.

Unless otherwise indicated, weight percentage is in reference to weight percentage of the composition. All temperatures, unless otherwise indicated are in Celsius.

Hydrophilically Modified Polyol Compounds

As used herein "tune" means having the ability to manipulate the chemical structure of the polyol compounds to achieve desired chemical characteristics. For example, an ethoxylated polyol compound modified by comprising an anionic capping unit and/or a cationic capping unit is a tuned structure giving desired characteristics for specific formulability and performance requirements.

The hydrophilically modified polyol compounds useful in the present invention comprises from 5 to 11 hydroxy moieties, further 5 to 10 hydroxy moieties, further from 6 to 9 hydroxy moieties. Suitable polyol compounds for starting materials for use in the present compositions include maltitol, sucrose, xylitol, pentaerythitol, glucose, maltose, matotriose, maltodextrin, maltopentose, maltohexose, isomaltulose, sorbitol, xylan, polyglycerol, diglycerol ether and mixtures thereof. Good examples include the polyol compound being selected as sorbitol, maltitol, and mixtures thereof.

At least one of the hydroxy moieties of the polyol compound further comprises one or more ethoxy moieties. The average degree of ethoxylation of individual hydroxy moieties is from about 1 to about 100, preferably from about 5 to about 40, more preferably from about 10 to about 35 per hydroxy moiety.

The modified polyol compounds useful in the present invention further have at least one of the ethoxy moieties comprising at least one anionic capping unit. Suitable anionic capping unit include sulfate, sulfosuccinate, succinate, maleate, sulphonate, methylene carboxylate, ethylene carboxylate, phosphate, phosphate, polyphosphate and mixtures thereof. Preferably the anionic capping units are sulfate and/or sulfonate.

The hydrophilically modified polyol compounds useful in the present invention further have at least one of the ethoxy moieties comprising at least one cationic capping unit. Suitable cationic capping units include amine capping units. The amine capping unit is selected from a primary amine containing capping unit, a secondary amine containing capping unit, a tertiary amine containing capping unit, and mixtures thereof.

Suitable primary amines for the primary amine containing capping unit include monoamines, diamine, triamine, polyamines, and mixtures thereof. Suitable secondary amines for the secondary amine containing capping unit include monoamines, diamine, triamine, polyamines, and mixtures thereof. Suitable tertiary amines for the tertiary amine containing capping unit include monoamines, diamine, triamine, polyamines, and mixtures thereof.

Suitable monoamines, diamines, triamines or polyamines for use in the present invention include ammonia, methyl amine, dimethylamine, ethylene diamine, N,-N'-dimethylaminopropylamine, N,N-dimethylaminopropylamine, hexemethylene diamine, ethylamine, diethylamine, dodecylamine, N-methyldodecylamine, diisopropylamine, methoxypropylamine, N-methyl-N-ethylamine, bis dimethylaminopropylamine (bis DMAPA), benzylamine, isoquinoline, tallow triethylenediamine, mono substituted monoarnine, monosubstituted diamine, monosubstituted polyamine, disubstituted monoamine, disubstiuted diamine, disubstituted polyamine, trisubstituted triamine, tri-substituted polyamine, multisubstituted polyamine comprising more than three substitutions provided at least one nitrogen contains a hydrogen, and mixtures thereof.

In another embodiment of the present invention, at least one of nitrogens in the amine capping unit is quaternized. As used herein "quaternized" means that the amine capping unit is given a positive charge through quaternization or protonization of the amine capping unit. For example, bis-DMAPA contains three nitrogens, only one of the nitrogens need be quaternized.

In an embodiment, one or more hydroxy moieties further comprise an ethoxy moiety having an anionic capping unit and one or more hydroxy moiety having a cationic capping unit. For example in formula (I) and formula (II):

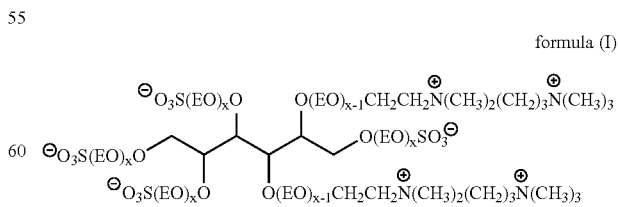

formula (I)

wherein x of formula (I) is from about 1 to about 100, or such as from about 5 to about 40, or such as from about 10 to about 35. EO represents an ethoxy moiety.

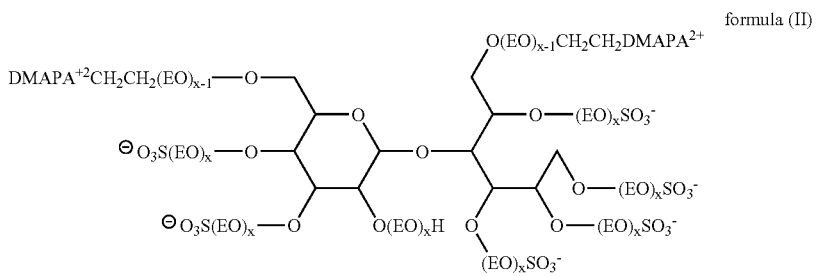

formula (II)

wherein x of formula (II) is from about 1 to about 100, or such as from about 5 to about 40, or such as from about 10 to about 35. DMAPA is dimethylaminopropyl amine. EO represents an ethoxy moiety.

Further examples are included in Table 1 below. The individual hydrophilically modified polyol compounds may also be mixtures of the examples below. The starting polyol compound is indicated as the "backbone" in Table 1. Several examples may be achieved similar to that shown for sorbitol in formula (I) and maltitol in formula (II) with x for formula (I) and formula (II) being as defined above.

TABLE 1

| Backbone | # of OH-groups (arms) | # EO/hydroxyl moiety | # anionic capping unit | # of cationic capping unit |
|---|---|---|---|---|
| sorbitol | 6 | x | 6 | 0 |
| sorbitol | 6 | x | 5 | 0-1 |
| sorbitol | 6 | x | 4 | 0-2 |
| sorbitol | 6 | x | 3 | 0-3 |
| sorbitol | 6 | x | 2 | 0-4 |
| sorbitol | 6 | x | 1 | 0-5 |
| sorbitol | 6 | x | 0 | 0-6 |
| maltitol | 9 | x | 9 | 0 |
| maltitol | 9 | x | 8 | 0-1 |
| maltitol | 9 | x | 7 | 0-2 |
| maltitol | 9 | x | 6 | 0-3 |
| maltitol | 9 | x | 5 | 0-4 |
| maltitol | 9 | x | 4 | 0-5 |
| maltitol | 9 | x | 3 | 0-6 |
| maltitol | 9 | x | 2 | 0-7 |
| maltitol | 9 | x | 1 | 0-8 |
| maltitol | 9 | x | 0 | 0-9 |

Furthermore it is preferred the overall average charge on the hydrophilically modified polyol compound is from about +4 to about −4, more preferably from about +3 to about −3, even more preferably from about −2 to about 2 and from even more preferable from about +1 to about −1. As used herein "overall charge" is being defined by the following formula (III):

Overall average charge=Σ average positive charges−Σaverage negative charges   formula (III)

One of skill will note that a distribution of materials may be present, so materials having no anionic and no cationic capping units may be present and still obtain an overall average charge between that indicated above. One of skill will also recognize that the cationic capping unit may comprise have more than one positive charge.

Process of Making

A process for making the hydrophilically modified polyol compound of the present invention comprises the optional step of ethoxylating a polyol compound comprising 5 to 11 hydroxy moieties such that the average degree of ethoxylation of at least one hydroxy moiety is between about 1 and about 100; and such as from about 5 to about 40; further such as from about 10 to about 35; to form an ethoxylated polyol comprising at least one ethoxy moiety. Alternatively, an ethoxylated polyol, such as CAS 52625-13-5, may be used as the starting material.

If the average degree of ethoxylation is not a desired level, an ethoxylation step may be used to achieve the desired degree of ethoxylation from about 1 to about 100, and such as from about 5 to about 40; further such as from about 10 to about 35.

Next, the process comprises the step of reacting at least one ethoxy moiety of the compound with an anionic capping unit to form an anionic ethoxylated polyol, although more anionic capping units may be selected. The at least one anionic capping unit selected from one of the following anionic groups; sulfate, sulfonate, and mixtures thereof; to form an anionic ethoxylated polyol. The process may partially or complete such that the ethoxy moiety of the ethoxylated polyol comprises from 20% to 100%, preferably from 30% to 100%, preferably from 50% to 90%, and more preferably from 60% to 80% of the ethoxy moieties an anionic capping unit. The sulfation process for the anionic ethoxylated polyol may be via falling film sulfur trioxide, chlorosulfonic acid or via the addition of sulfuric acid as described in U.S. application Ser. No. 60/554576, filed Mar. 19, 2004, published as US 2005/0209476 A1.

Next the process consists of displacement of some or all of the anionic capping units with nitrogen containing cationic capping units and optionally quaternizing the nitrogen containing cationic capping unit to form a zwitterionic polymer as described in the U.S. provisional application No. 60/531385 filed Dec. 19, 2003, published as WO 05/063847. Preferred cationic capping units are selected from amine capping units; the amine capping units are selected from dimethylamine, ethylene diamine, dimethylaminopropylamine, bis dimethylaminopropylamine (bis DMAPA), and hexamethylene diamine.

Ethoxylation of a Polyol

Ethoxylation of Sorbitol to Form Sorbitol 19 EO 2DMAPA 3-4 $SO_3^-$

Ethoxylation (EO) of a polyol, such as sorbitol, may be completed by any known technique, such as that described in EP 174436 A1 Add sorbitol (17.5 g, 0.0962 mol) to an autoclave, purge the autoclave with nitrogen, heat sorbitol to 110-120° C.; autoclave stirred and apply vacuum to about 20 mmHg.

Continuously apply vacuum while cooling the autoclave to about 110-120° C. Introduce 6.2 g of a 25% sodium methoxide in methanol solution (0.0288 moles) to achieve a 5% catalyst loading based upon hydroxy moieties. Remove the methanol from the methoxide solution under vacuum from the autoclave. Use a device to monitor the power consumed by the agitator. Monitor the agitator power along with the temperature and pressure. The agitator power and temperature values will gradually increase as methanol is removed from the autoclave and the viscosity of the mixture will increases and stabilizes in about 1.5 hours thereby indicating that most of the methanol is removed. Further heat and agitate under vacuum the mixture for an additional 30 minutes.

Remove the vacuum and cool the autoclave to or kept at 110° C. while charging the autoclave with nitrogen gas to 1725 kPa (250 psia) and then vent the autoclave to ambient pressure. Charge the autoclave to 1380 kPa (200 psia) with nitrogen gas. Add 483 g (10.97 mol, resulting in a total of 19 moles of ethylene oxide (EO) per mol of OH) ethylene oxide to the autoclave incrementally while closely monitoring the autoclave pressure, temperature, and ethylene oxide flow rate. Maintain the temperature between 110 and 120° C. and limit any temperature increase due to reaction exotherm. After the addition of the ethylene oxide, increase the temperature to 120° C. and stir the mixture for an additional 2 hours.

Collect the reaction mixture into a 22 L three neck round bottomed flask purged with nitrogen gas. Neutralize the strong alkali catalyst by the slow addition of 2.8 g methanesulfonic acid (0.0288 moles) with heating (110° C.) and mechanical stirring. Purge the reaction mixture of residual ethylene oxide and deodorized by sparging an inert gas (argon or nitrogen) into the mixture through a gas dispersion frit while agitating and heating the mixture to 120° C. for 1 hour. Cool slightly the final reaction product, approximately 500 g, and pour into a glass container purged with nitrogen gas for storage.

Alternatively, a polyol may be purchased with a degree of ethoxylation that is at or below that desired, such as CAS 52625-13-5, sorbitol polyoxy ethylene ether available from Lipo Chemicals Inc. Wherein the desired degree of ethoxylation is achieved by the processes known and/or described above.

Sulfation of Sorbitol EO114 (Average of 19 EO Moieties Per Hydroxy Moiety)

Weigh into a 500 ml Erlenmeyer flask Sorbitol E114 (299.7 g, 0.058 mol) and methylene chloride (300 g) ("the solution"). Equip the flask with a magnetic stirring bar and stir until complete dissolution. Place the flask in an ice bath until the solution reaches about 10° C. Stir vigorous while slowing pouring chlorosulfonic acid (48.3 g, 0.415 mol) over the period of about 5 minutes to form a reaction solution. Stir the reaction solution in the ice bath for 1.5 hours.

Place a solution of sodium methoxide (197 g of 25% in methanol) in 50 g of methylene chloride in a 1 L Erlenmeyer flask ("base solution") and chill in an ice bath until the temperature of the solution reaches about 10° C. Stir the base solution vigorous using a magnetic stirring bar. Slowly pour the reaction solution into the base solution over a period of about 3 minutes. A mild exotherm should be observed. The resulting solution becomes milky as salts form. After addition is complete, measure the pH to be about 12. Add to this resulting solution about 100 ml of distilled water, and transfer the resulting emulsion to a 1 L round bottom flask and use a rotary evaporator at 50° C. to strip, in portions, to obtain a clear solution. Transfer the clear solution to a Kulgelrohr apparatus. At 60° C. and 133 Pa (1 mm Hg) strip the solution to yield 366 g of off-white waxy solid, 90% active (10% salts).

Carbon NMR spectrum (500 MHz; pulse sequence: s2pu1, solvent D2O; relax. delay 0.300 sec, pulse 45.0; acq. time 1.090 sec) shows an absence of alcohol groups at about 60 ppm and the emergence of a new peak at about 67 ppm consistent with formation of the end group sulfate. Proton NMR spectrum (500 MHz or 300 MHz; pulse sequence: s2pu1, solvent D2O; relax. delay 1.000 sec, pulse 45.0; acq. time 2.345 sec) shows a new peak at about 4 ppm which was integrated against the ethoxy group protons at about 3.5 ppm and is consistent with the molecule having 6 end group sulfates.

Amination of Sorbitol EO114 Hexasulfate

Weigh into a 200 ml glass liner sorbitol EO114 hexasulfate (61.3 g of 90% active, 0.0095 mol) and 3-(dimethylamino)propylamine ("DMAPA" 18.5 g, 0.181 mol). Heat the liner in a rocking autoclave at 152 kPa (150 psig) under nitrogen until the temperature reaches 165° C. and hold at 165° C. for 2 hours. Cool to room temperature (20° C.-25° C.). Take the material up in 150 ml of methylene chloride and centrifuge to separate the salts. Transfer the supernatant to a 500 ml round bottom flask and strip the supernatant on a rotary evaporator at 50° C. until most (less than 5 mL) of the solvent is removed. Heat on a Kugelrohr apparatus at 120° C. and 133 Pa (1 mm Hg) for 30 minutes to remove excess amine to afford 47.8 g of brown hard solid. Proton NMR (500 MHz or 300 MHz; pulse sequence: s2pu1, solvent $D_2O$; relax. delay 0.300 sec, pulse 45.0; acq. time 3.744 sec) indicated about 3 sulfates and about 2 DMAPA per molecule.

EXAMPLE 3

Quaternization of Amine Containing Sulfate of Example 2

Dissolve 100 g of an aminated Sorbitol EO114 in 100 g of methylene chloride in a 500 ml round bottom flask equipped with a magnestic stirring bar and chill in an ice bath until the temperature reaches 10° C. Adjust the solution to a pH 12 with sodium methoxide (25% solution in methanol). Add to the solution methyl iodide (15.0 g, 0.106 mol). Stopper the flask and stir the solution overnight (about 14 hours). Strip the solution on a Kugelrohr apparatus at 50° C. and 133 Pa (1 mm Hg) to afford 66 g of tacky brown solid. Proton NMR (500 MHz or 300 MHz; pulse sequence: s2pu1, solvent $D_2O$; relax. delay 1.000 sec, pulse 45.0; acq. time 2.345 sec) indicated that all nitrogens in the amine capping unit were fully quaternized.

Ethoxylation of Maltitol to Form Maltitol EO 27 2DMAPA $5SO_3^-$

Ethoxylation (EO) of a polyol, such as maltitol may be completed by any known technique, such as that described in EP 174436 A1. Propoxylation may also be completed by known techniques.

Add Maltitol (50 g, 0.145 moles) to an autoclave followed by sodium methoxide (2.8 g, 0.0131 moles using 25% sodium methoxide in methanol solution, to achieve an overall 9 mole % catalyst level, or 1 mole % per hydroxy moiety) to form a Maltitol mixture. Heat the Maltitol mixture to 150-160° C. while applying vacuum 2.67-4 kPa (20-30 mmHg) to remove methanol. Apply stirring once the Maltitol mixture has melted and agitate under vacuum for several hours (5-15 hours) until the methanol has been completely removed.

Add ethylene oxide (EO) to the autoclave incrementally while closely monitoring the autoclave pressure and temperature while limiting any temperature increases due to reaction exotherm. Cool the temperature to 110-120° C. after the addition of 287 g of ethylene oxide (6.53 moles, resulting in a total of 5 moles of ethylene oxide per mol of hydroxy moiety (—OH)) before adding additional ethylene oxide (1263 g, 28.7 mol, resulting in a total of 27 ethylene oxide per mole hydroxy moiety (—OH)). Stir the mixture for 2 hours after all the ethylene oxide has been consumed; as indicated by no change in the pressure reading.

Collect the reaction mixture into a 5 L three neck round bottomed flask that is purged with nitrogen gas. Neutralize the strong alkali catalyst by slow addition of 1.3 g methanesulfonic acid (0.0131 moles) with heating (110° C.) and mechanical stirring. Purge the reaction mixture is of residual ethylene oxide and deodorized by sparging an inert gas (argon or nitrogen) into the mixture through a gas dispersion frit while agitating and heating the mixture to 120° C. for 1 hour. The final reaction product, approximately 1600 g, is cooled slightly, and poured into a glass container then purged with nitrogen for storage.

Sulfation of Maltitol EO 27

Weigh into a 250 ml Erlenmeyer flask Maltitol EO27 (25 g, 0.0023 mol) and methylene chloride (40 g) ("the solution"). Equip the flask with a magnetic stirring bar and stir until complete dissolution. Place the flask in an ice bath until the solution reaches about 10° C. Stir vigorous while slowing pouring chlorosulfonic acid (2.3 g, 0.020 mol) over the period of about 5 minutes to form a reaction solution. Stir the reaction solution in the ice bath for 1.5 hours.

Place a solution of sodium methoxide (9 g of 25% in methanol) in 20 g of methylene chloride in a 500 ml Erlenmeyer flask ("base solution") and chill in an ice bath until the temperature of the solution reaches about 10 C. Stir the base solution vigorous using a magnetic stirring bar. Slowly pour the reaction solution into the base solution over a period of about 3 minutes. A mild exotherm should be observed. The resulting solution becomes milky as salts form. After addition is complete, measure the pH to be about 12. Add to this resulting solution about 50 ml of distilled water, and transfer the resulting emulsion to a 1 L round bottom flask and use a rotary evaporator at 50° C. to strip, in portions, to obtain a clear solution. Transfer the clear solution to a Kulgelrohr apparatus. At 60 C and 133 Pa (1 mm Hg) strip the solution to yield 28 g of off-white waxy solid, 95% active (5% salts).

Amination of Maltitol 27 EO 8.7 Sulfate

Weigh into a 10 ml high-pressure mini-reactor equipped with a magnetic stirring bar Maltitol EO27, 8.5 sulfate (4.3 g, 0.0031 mol sulfate) as prepared and described above; and 3-dimethylamino-1-propylamine (DMAPA, 1.1 g, 0.0108 mol). Place the reactor in a Reacti-Therm® apparatus and heat to about 170° C. over about 1.5 hours. Stir the reaction at 170° C. for 2.5 hours. Cool cooling to room temperature. Take up the reaction mixture in about 20 ml of methylene chloride and centrifuge to remove any salts that are present. Strip the supernatant on a rotary evaporator (50° C.) followed by a Kugelrohr (160° C. for 1.5 hours at about 267 Pa (2 mm Hg)) to afford 3.5 g of light brown soft solid.

Dissolve this light brown soft solid material in about 20 g of methylene chloride and adjusted to a pH of about 10 with 25% sodium methoxide in methanol. Add to the solution iodomethane (0.3 g, 0.0021 mol). Stopper the flask and stir the solution at room temperature (20° C.-25° C.) for 1 hour. The pH should be measured at about 7. Add additional sodium methoxide to bring the pH to about 10, and add additional iodomethane (0.3 g, 0.0021 mol). Stir the solution at room temperature (20° C.-25° C.) overnight (about 12 hours). Strip the solution on a rotary evaporator (50° C.) followed by a Kugelrohr (70° C. for 1 hour at about 267 Pa (2 mm Hg)) to afford 3.9 g of orange oily material. Proton and carbon NMR spectra indicate the presence of 5.1 sulfate groups and 2.5 quaternized DMAPA groups per molecule.

The composition of the present invention may comprise from about 0.005% to about 30%, and such as from about 0.01% to about 10%, further such as from about 0.05% to about 5% by weight of the composition of a hydrophilically modified polyol compound as described herein.

Surfactant System

The composition of the present invention comprises a surfactant system comprising $C_{10}$-$C_{15}$ alkyl benzene sulfonates (LAS) and one or more co-surfactants selected from nonionic, cationic, anionic or mixtures thereof.

The selection of co-surfactant may be dependent upon the desired benefit. In one embodiment, the co-surfactant is selected as a nonionic surfactant, preferably $C_{12}$-$C_{18}$ alkyl ethoxylates. In another embodiment, the co-surfactant is selected as an anionic surfactant, preferably $C_{10}$-$C_{18}$ alkyl alkoxy sulfates ($AE_xS$) wherein x is from 1-30. In another embodiment the co-surfactant is selected as a cationic surfactant, preferably dimethyl hydroxyethyl lauryl ammonium chloride.

$C_{10}$-$C_{15}$ Alkyl Benzene Sulfonates (LAS)

The surfactant system comprises $C_{10}$-$C_{15}$ alkyl benzene sulfonates (LAS) from about 9% to about 25%, or from about 13% to about 25%, or from about 15% to about 23% by weight of the composition. The surfactant system further comprises from 0% to about 7%, or from about 0.1% to about 5%, or from about 1% to about 4% by weight of the composition of a co-surfactant selected from a nonionic co-surfactant, cationic co-surfactant, anionic co-surfactant and any mixture thereof.

Nonionic Co-Surfactants

Non-limiting examples of nonionic co-surfactants include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates such as PLURONIC® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, $BAE_x$, wherein x is from 1-30, as discussed in U.S. Pat. No. 6,153,577, U.S. Pat. No. 6,020,303 and U.S. Pat. No. 6,093,856; Alkylpolysaccharides as discussed in U.S. Pat. No. 4,565,647 Llenado, issued Jan. 26, 1986; specifically alkylpolyglycosides as discussed in U.S. Pat. No. 4,483,780 and U.S. Pat. No. 4,483,779; Polyhydroxy fatty acid amides (GS-base) as discussed in U.S. Pat. No. 5,332,528; and ether capped poly(oxyalkylated) alcohol surfactants as discussed in U.S. Pat. No. 6,482,994 and WO 01/42408.

Non-limiting examples of semi-polar nonionic co-surfactants include: water-soluble amine oxides containing one alkyl moiety of from about 10 to about 18 carbon atoms and 2 moieties selected from the group consisting of alkyl moieties and hydroxyalkyl moieties containing from about 1 to about 3 carbon atoms; water-soluble phosphine oxides containing one alkyl moiety of from about 10 to about 18 carbon atoms and 2 moieties selected from the group consisting of alkyl moieties and hydroxyalkyl moieties containing from about 1 to about 3 carbon atoms; and water-soluble sulfoxides containing one alkyl moiety of from about 10 to about 18 carbon atoms and a moiety selected from the group consisting of alkyl moieties and hydroxyalkyl moieties of from about 1 to about 3 carbon atoms. See WO 01/32816, U.S. Pat. No. 4,681,704, and U.S. Pat. No. 4,133,779.

Cationic Co-Surfactants

Non-limiting examples of cationic co-surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, specifically amido propyldimethyl amine (APA).

Anionic Co-Surfactants

Nonlimiting examples of anionic co-surfactants useful herein include: $C_{10}$-$C_{20}$ primary, branched chain and random alkyl sulfates (AS); $C_{10}$-$C_{18}$ secondary (2,3) alkyl sulfates; $C_{10}$-$C_{18}$ alkyl alkoxy sulfates (AE$_x$S) wherein x is from 1-30; $C_{10}$-$C_{18}$ alkyl alkoxy carboxylates comprising 1-5 ethoxy units; mid-chain branched alkyl sulfates as discussed in U.S. Pat. No. 6,020,303 and U.S. Pat. No. 6,060,443; mid-chain branched alkyl alkoxy sulfates as discussed in U.S. Pat. No. 6,008,181 and U.S. Pat. No. 6,020,303; modified alkylbenzene sulfonate (MLAS) as discussed in WO 99/05243, WO 99/05242 and WO 99/05244; methyl ester sulfonate (MES); and alpha-olefin sulfonate (AOS).

Composition

The present invention relates to a composition comprising the modified alkoxylated polyol compound and a surfactant system comprising $C_8$-$C_{18}$ linear alkyl sulphonate surfactant and a co-surfactant. The compositions can be in any form, namely, in the form of a liquid; a solid such as a powder, granules, agglomerate, paste, tablet, pouches, bar, gel; an emulsion; types delivered in dual-compartment containers; a spray or foam detergent; premoistened wipes (i.e., the cleaning composition in combination with a nonwoven material such as that discussed in U.S. Pat. No. 6,121,165, Mackey, et al.); dry wipes (i.e., the cleaning composition in combination with a nonwoven materials, such as that discussed in U.S. Pat. No. 5,980,931, Fowler, et al.) activated with water by a consumer; and other homogeneous or multiphase consumer cleaning product forms.

The compositions may be also suitable for use or incorporation into industrial cleaners (i.e. floor cleaners). In one embodiment, the cleaning composition of the present invention is a liquid or solid laundry detergent composition. In another embodiment, the cleaning composition of the present invention is a hard surface cleaning composition, preferably wherein the hard surface cleaning composition impregnates a nonwoven substrate. As used herein "impregnate" means that the hard surface cleaning composition is placed in contact with a nonwoven substrate such that at least a portion of the nonwoven substrate is penetrated by the hard surface cleaning composition, preferably the hard surface cleaning composition saturates the nonwoven substrate.

In another embodiment the cleaning composition is a liquid dish cleaning composition, such as liquid hand dishwashing compositions, solid automatic dishwashing cleaning compositions, liquid automatic dishwashing cleaning compositions, and tab/unit does forms of automatic dishwashing cleaning compositions.

The cleaning composition may also be utilized in car care compositions, for cleaning various surfaces such as hard wood, tile, ceramic, plastic, leather, metal, glass. This cleaning composition could be also designed to be used in a personal care and pet care compositions such as shampoo composition, body wash, liquid or solid soap and other cleaning composition in which surfactant comes into contact with free hardness and in all compositions that require hardness tolerant surfactant system, such as oil drilling compositions.

A process of making the composition of the present invention comprising the steps of:

(a) hydrophilically modifying a polyol compound such that the overall charge is from about +3 to about −3, resulting in a hydrophilically modified polyol compound;

(b) mixing the hydrophilically modified polyol compound with a surfactant system comprising from about 13% to about 25% by weight of the composition of $C_{10}$-$C_{15}$ linear alkyl benzene sulfonate of a co-surfactant selected from nonionic surfactants, anionic surfactants, cationic surfactants, and mixtures thereof.

Further cleaning adjunct materials may be added in an optional step for the process. Hydrophilically modifying a polyol compound may be any tuning discussed above via the ethoxylation and selecting an anionic capping unit, a cationic capping unit, or mixtures thereof.

Cleaning Adjunct Materials

In general, a cleaning adjunct is any material required to transform a composition containing only the minimum essential ingredients into a composition useful for laundry, hard surface, personal care, consumer, commercial and/or industrial cleaning purposes. In certain embodiments, cleaning adjuncts are easily recognizable to those of skill in the art as being absolutely characteristic of cleaning products, especially of cleaning products intended for direct use by a consumer in a domestic environment.

The precise nature of these additional components, and levels of incorporation thereof, will depend on the physical form of the cleaning composition and the nature of the cleaning operation for which it is to be used.

The cleaning adjunct ingredients if used with bleach should have good stability therewith. Certain embodiments of cleaning compositions herein should be boron-free and/or phosphate-free as required by legislation. Levels of cleaning adjuncts are from about 0.00001% to about 99.9%, and such as from about 0.0001% to about 50% by weight of the cleaning compositions. Use levels of the overall cleaning compositions can vary widely depending on the intended application, ranging for example from a few ppm in solution to so-called "direct application" of the neat cleaning composition to the surface to be cleaned.

Quite typically, cleaning compositions herein such as laundry detergents, laundry detergent additives, hard surface cleaners, synthetic and soap-based laundry bars, fabric softeners and fabric treatment liquids, solids and treatment articles of all kinds will require several adjuncts, though certain simply formulated products, such as bleach additives, may require only, for example, an oxygen bleaching agent and a surfactant as described herein. A comprehensive list of suitable laundry or cleaning adjunct materials can be found in WO 99/05242.

Common cleaning adjuncts include builders, enzymes, polymers not discussed above, bleaches, bleach activators, catalytic materials and the like excluding any materials already defined hereinabove. Other cleaning adjuncts herein can include suds boosters, suds suppressors (antifoams) and the like, diverse active ingredients or specialized materials such as dispersant polymers (e.g., from BASF Corp. or Rohm & Haas) other than those described above, color speckles, silvercare, anti-tarnish and/or anti-corrosion agents, dyes, fillers, germicides, alkalinity sources, hydrotropes, anti-oxidants, enzyme stabilizing agents, pro-perfumes, perfumes, solubilizing agents, carriers, processing aids, pigments, and, for liquid formulations, solvents, chelating agents, dye transfer inhibiting agents, dispersants, brighteners, suds suppressors, dyes, structure elasticizing agents, fabric softeners, anti-abrasion agents, hydrotropes, processing aids, and other fabric care agents, surface and skin care agents. Suitable examples of such other cleaning adjuncts and levels of use are found in U.S. Pat. Nos. 5,576,282, 6,306,812 B1 and 6,326,348 B1.

Method of Use

The present invention includes a method for cleaning a targeted surface. As used herein "targeted surface" may include such surfaces such as fabric, dishes, glasses, and other cooking surfaces, hard surfaces, hair or skin. As used herein "hard surface" includes hard surfaces being found in a typical home such as hard wood, tile, ceramic, plastic, leather, metal, glass. Such method includes the steps of contacting the composition comprising the modified polyol compound, in neat form or diluted in wash liquor, with at least a portion of a targeted surface then optionally rinsing the targeted surface. Preferably the targeted surface is subjected to a washing step prior to the aforementioned optional rinsing step. For purposes of the present invention, washing includes, but is not limited to, scrubbing, wiping and mechanical agitation.

As will be appreciated by one skilled in the art, the cleaning compositions of the present invention are ideally suited for use in home care (hard surface cleaning compositions), personal care and/or laundry applications.

The composition solution pH is chosen to be the most complimentary to a target surface to be cleaned spanning broad range of pH, from about 5 to about 11. For personal care such as skin and hair cleaning pH of such composition preferably has a pH from about 5 to about 8 for laundry cleaning compositions pH of from about 8 to about 10. The compositions are preferably employed at concentrations of from about 200 ppm to about 10,000 ppm in solution. The water temperatures preferably range from about 5° C. to about 100° C.

For use in laundry cleaning compositions, the compositions are preferably employed at concentrations from about 200 ppm to about 10000 ppm in solution (or wash liquor). The water temperatures preferably range from about 5° C. to about 60° C. The water to fabric ratio is preferably from about 1:1 to about 20:1.

The method may include the step of contacting a nonwoven substrate impregnated with an embodiment of the composition of the present invention As used herein "nonwoven substrate" can comprise any conventionally fashioned nonwoven sheet or web having suitable basis weight, caliper (thickness), absorbency and strength characteristics. Examples of suitable commercially available nonwoven substrates include those marketed under the tradename SONTARA® by DuPont and POLYWEB® by James River Corp.

As will be appreciated by one skilled in the art, the cleaning compositions of the present invention are ideally suited for use in liquid dish cleaning compositions. The method for using a liquid dish composition of the present invention comprises the steps of contacting soiled dishes with an effective amount, typically from about 0.5 ml. to about 20 ml. (per 25 dishes being treated) of the liquid dish cleaning composition of the present invention diluted in water.

Formulations

TABLE 2

Granular Laundry Detergent

| | A wt % | B wt % | C wt % | D wt % | E wt % |
|---|---|---|---|---|---|
| $C_{11-12}$ Linear alkyl benzene sulphonate | 13-25 | 13-25 | 13-25 | 13-25 | 9-25 |
| $C_{12-18}$ Ethoxylate Sulfate | — | — | 0-3 | — | 0-1 |
| $C_{14-15}$ alkyl ethoxylate (EO = 7) | 0-3 | 0-3 | — | 0-5 | 0-3 |
| Dimethyl hydroxyethyl lauryl ammonium chloride | — | — | 0-2 | 0-2 | 0-2 |
| Sodium tripolyphosphate | 20-40 | — | 18-33 | 12-22 | 0-15 |
| zeolite | 0-10 | 20-40 | 0-3 | — | — |
| silicate builder | 0-10 | 0-10 | 0-10 | 0-10 | 0-10 |
| Carbonate | 0-30 | 0-30 | 0-30 | 5-25 | 0-20 |
| diethylene triamine penta acetate | 0-1 | 0-1 | 0-1 | 0-1 | 0-1 |
| polyacrylate | 0-3 | 0-3 | 0-3 | 0-3 | 0-3 |
| Carboxy Methyl Cellulose | 0.2-0.8 | 0.2-0.8 | 0.2-0.8 | 0.2-0.8 | 0.2-0.8 |
| Polymer[1] | 1-5 | 1-5 | 1-5 | 1-5 | 1-5 |
| Percarbonate | 0-10 | 0-10 | 0-10 | 0-10 | 0-10 |
| nonanoyloxybenzenesulfonate | — | — | 0-2 | 0-2 | 0-2 |
| tetraacetylethylenediamine | — | — | 0-0.6 | 0-0.6 | 0-0.6 |
| Zinc Phthalocyanine Tetrasulfonate | — | — | 0-0.005 | 0-0.005 | 0-0.005 |
| Brightener | 0.05-0.2 | 0.05-0.2 | 0.05-0.2 | 0.05-0.2 | 0.05-0.2 |
| $MgSO_4$ | — | — | 0-0.5 | 0-0.5 | 0-0.5 |
| ENZYMES | 0-0.5 | 0-0.5 | 0-0.5 | 0-0.5 | 0-0.5 |

TABLE 2-continued

Granular Laundry Detergent

| | A wt % | B wt % | C wt % | D wt % | E wt % |
|---|---|---|---|---|---|
| MINORS (perfume, dyes, suds stabilizers) | balance | balance | balance | balance | balance |

[1]A polymer or any mixture of polymers according to any of the Examples from Table 1.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
   a) from about 0.005% to about 30% of one or more hydrophilically modified polyol compounds comprising from 5 to 11 hydroxy moieties, wherein at least one hydroxy moiety further comprises one or more ethoxy moiety; the one or more ethoxy moiety further comprising an anionic capping unit, a cationic capping unit, or a mixture thereof; wherein the overall average charge on the hydrophilically modified polyol compound is about −4 to about +4; and wherein the hydrophilically modified polyol compound is derived from maltitol, sucrose, xylitol, pentaerythritol, glucose, maltose, matotriose, maltodextrin, maltopentose, maltohexose, isomaltulose, sorbitol, xylan, polyglycerol, diglycerol ether and mixtures thereof; cationic surfactants, cationic ester surfactants, and amino surfactants, specifically amido propyldimethyl amine.

2. A composition of claim 1 wherein the modified polyol compound comprises from 5 to 10 hydroxy moieties.

3. A composition of claim 1 wherein the modified polyol compound comprises from 6 to 9 hydroxy moieties.

4. A composition of claim 1 wherein the hydrophilically modified polyol compound further comprises one or more ethoxy moieties further comprising the anionic capping unit.

5. A composition of claim 1 wherein the hydrophilically modified polyol compound further comprises one or more ethoxy moieties further comprising the cationic capping unit.

6. A composition of claim 1 wherein the hydrophilically modified polyol compound further comprises one or more ethoxy moieties further comprising the anionic capping unit and one or more ethoxy moieties further comprising the cationic capping unit.

7. A composition of claim 1 wherein the cationic capping unit is selected from an amine capping unit.

8. A composition of claim 1 wherein the anionic capping unit is selected from the group consisting of sulfate, sulfosuccinate, succinate, maleate, sulphonate, methylene carboxylate, ethylene carboxylate, phosphate, polyphosphate and mixtures thereof.

9. A composition of claim 8 wherein the anionic capping unit is selected from the group consisting of sulfate, sulfonate, methylene carboxylate and ethylene carboxylate.

10. A composition of claim 1 wherein the hydrophilically modified polyol compound has an overall charge from about +3 to about −3.

11. A composition of claim 1 wherein the hydrophilically modified polyol compound has an overall charge from about +1 to about −1.

12. A composition according to claim 1 wherein the co-surfactant is a cationic surfactant.

13. A composition of claim 1 wherein the co-surfactant is selected as a nonionic surfactant.

14. A composition according to claim 1 further comprising an anionic co-surfactant.

15. A composition of claim 14 wherein the anionic co-surfactant is selected from the group consisting of: $C_{10}$-$C_{20}$ primary, branched chain and random alkyl sulfates; $C_{10}$-$C_{18}$ secondary (2,3) alkyl sulfates; $C_{10}$-$C_{18}$ alkyl alkoxy sulfates; $C_{10}$-$C_{18}$ alkyl alkoxy carboxylates comprising 1-5 ethoxy units; mid-chain branched alkyl sulfates; mid-chain branched alkyl alkoxy sulfates; modified alkylbenzene sulfonate; methyl ester sulfonate; and alpha-olefin sulfonate.

16. A composition of claim 1 wherein the composition is in the form of a liquid detergent composition.

17. A composition of claim 1 wherein the composition is in the form of a solid detergent composition selected from the group consisting of a powder, granules, agglomerate, paste, tablet, pouches, bar, and gel.

18. A method of cleaning a targeted surface comprising the stems of identifying a targeted surface to be cleaned and contacting the composition of claim 1 with the targeted surface.

19. A composition of claim 7 wherein the amine capping unit is selected from the group consisting of ammonia, methyl amine, dimethylamine, ethylene diamine, N,—N'-dimethylaminopropylamine, N,N-dimethylaminopropylamine, hexemethylene diamine, ethylamine, diethylamine, dodecylamine, N-methyldodecylamine, diisopropylamine, methoxypropylamine, N-methylamine, and mixtures thereof.

20. A process of making the composition of claim 1, comprising the steps of:
   a) hydrophilically modifying the polyol compound; and
   b) a surfactant system comprising from about 9% to about 25% by weight of the composition of a C10-C15 linear alkyl benzene sulfonate and from 0.01% to about 7% by weight of the composition of a co-surfactant selected from the group consisting of nonionic surfactants, cationic surfactants, and mixtures thereof;
   wherein the nonionic surfactant is selected from the group consisting of C12-C18 alkyl ethoxylates; C6-C12 alkyl phenol alkoxylates, wherein the alkoxylate units are a mixture of ethyleneoxy and propyleneoxy units; C12-C18 alcohol and C6-C12 alkyl phenol condensates with ethylene oxide/propylene oxide block alkyl polyamine, ethoxylates; C14-C22 mid-chain branched alcohols; C14-C22 mid-chain branched alkyl alkoxylates; alkylpolysaccharides; polyhydroxy fatty acid amides; ether capped poly(oxyalkylated) alcohol surfactants; water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms;

and wherein the cationic surfactant is selected from the group consisting of alkoxylate quaternary ammonium surfactants, dimethyl hydroxyethyl quaternary ammonium surfactant, dimethyl hydroxyethyl lauryl ammonium chloride; polyamine b) mixing the hydrophilically modified polyol compound with the surfactant system.

21. The process of claim 20, wherein the hydrophilically modified polyol compound has an overall charge from about +3 to about --3.

* * * * *

UNITED STATES PATENT AND TRADEMARK OFFICE
CERTIFICATE OF CORRECTION

| | | |
|---|---|---|
| PATENT NO. | : 7,332,467 B2 | |
| APPLICATION NO. | : 11/303684 | |
| DATED | : February 19, 2008 | |
| INVENTOR(S) | : Schneiderman et al. | |

It is certified that error appears in the above-identified patent and that said Letters Patent is hereby corrected as shown below:

Title Page

After "( * ) Notice: Subject to any disclaimer, the term of this patent is extended or adjusted under 35 U.S.C. 154(b) by 0 days.", insert -- This patent is subject to a terminal disclaimer. --

Under (56) References Cited, U.S. PATENT DOCUMENTS, line 2, delete "4,661,228" and insert -- 4,661,288 --.

Column 4

Line 32, delete "monoarnine" and insert -- monoamine --.

Column 12

Line 22, after "weight of" insert -- and from 0% to about 7% by weight of the composition --.

Column 15

Delete Claim 1 and insert new Claim 1 as follows:

-- 1. A composition comprising:

a) from about 0.005% to about 30% of one or more hydrophilically modified polyol compounds comprising from 5 to 11 hydroxy moieties wherein at least one hydroxy moiety further comprises one or more ethoxy moiety; the one or more ethoxy moiety further comprising an anionic capping unit, a cationic capping unit, or a mixture thereof; wherein the overall average charge on the hydrophilically modified polyol compound is about -4 to about +4; and wherein the hydrophilically modified polyol compound is derived from maltitol, sucrose, xylitol, pentaerythitol, glucose, maltose, matotriose, maltodextrin, maltopentose, maltohexose, isomaltulose, sorbitol, xylan, polyglycerol, diglycerol ether and mixtures thereof;

Signed and Sealed this
Tenth Day of May, 2011

David J. Kappos
*Director of the United States Patent and Trademark Office* b) a surfactant system comprising from about 9% to about 25% by weight of the composition of $C_{10}$-$C_{15}$ linear alkyl benzene sulfonate and from 0.01% to about 7% by weight of the composition of a co-surfactant selected from the group consisting of nonionic surfactants, cationic surfactants, and mixtures thereof;

wherein the nonionic surfactant is selected from the group consisting of $C_{12}$-$C_{18}$ alkyl ethoxylates; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates; $C_{14}$-$C_{22}$ mid-chain branched alcohols; $C_{14}$-$C_{22}$ mid-chain branched alkyl alkoxylates; alkylpolysaccharides; polyhydroxy fatty acid amides; ether capped poly(oxyalkylated) alcohol surfactants; water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl moieties and hydroxyalkyl moieties of from about 1 to about 3 carbon atoms;

and wherein the cationic surfactant is selected from the group consisting of alkoxylate quaternary ammonium surfactants, dimethyl hydroxyethyl quaternary ammonium surfactant, dimethyl hydroxyethyl lauryl ammonium chloride; polyamine cationic surfactants, cationic ester surfactants, and amino surfactants specifically amido propyldimethyl amine. --

Column 16

Line 2 of Claim 18, delete "stems" and insert -- steps --.

Line 7 of Claim 19, delete "N-methylamine" and insert -- N-methyl-N-ethylamine --.

Columns 16, 17, 18

In Claim 20, delete the following section:

"b) a surfactant system comprising from about 9% to about 25% by weight of the composition of $C_{10}$-$C_{15}$ linear alkyl benzene sulfonate and from 0.01% to about 7% by weight of the composition of a co-surfactant selected from the group consisting of nonionic surfactants, cationic surfactants, and mixtures thereof;

wherein the nonionic surfactant is selected from the group consisting of $C_{12}$-$C_{18}$ alkyl ethoxylates; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates; $C_{14}$-$C_{22}$ mid-chain branched alcohols;

$C_{14}$-$C_{22}$ mid-chain branched alkyl alkoxylates; alkylpolysaccharides; polyhydroxy fatty acid amides; ether capped poly(oxyalkylated) alcohol surfactants; water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl moieties and hydroxyalkyl moieties of from about 1 to about 3 carbon atoms;

and wherein the cationic surfactant is selected from the group consisting of alkoxylate quaternary ammonium surfactants, dimethyl hydroxyethyl quaternary ammonium surfactant, dimethyl hydroxyethyl lauryl ammonium chloride; polyamine"